US008529831B1

(12) United States Patent
Ho et al.

(10) Patent No.: US 8,529,831 B1
(45) Date of Patent: Sep. 10, 2013

(54) SYSTEM AND METHOD FOR AIR PURIFICATION USING AN ENHANCED MULTI-FUNCTIONAL COATING BASED ON IN-SITU PHOTOCATALYTIC OXIDATION AND OZONATION

(75) Inventors: Wing Kei Ho, Hong Kong (HK); Jian Hui Huang, Hong Kong (HK)

(73) Assignees: Nano and Advanced Materials Institute Limited, Clear Water Bay (HK); Institute Company Limited, Clear Water Bay (HK)

( * ) Notice: Subject to any disclaimer, the term of this patent is extended or adjusted under 35 U.S.C. 154(b) by 0 days.

(21) Appl. No.: 13/577,912

(22) PCT Filed: Dec. 16, 2011

(86) PCT No.: PCT/CN2011/084156
§ 371 (c)(1),
(2), (4) Date: Aug. 9, 2012

(87) PCT Pub. No.: WO2012/079539
PCT Pub. Date: Jun. 21, 2012

Related U.S. Application Data

(60) Provisional application No. 61/457,058, filed on Dec. 17, 2010.

(51) Int. Cl.
*A61L 9/00* (2006.01)
*A61L 9/015* (2006.01)
*A61L 9/20* (2006.01)

(52) U.S. Cl.
USPC ...... 422/4; 422/5; 422/24; 422/120; 422/121; 422/122; 422/123

(58) Field of Classification Search
USPC .................... 422/122, 123, 120, 121, 4, 5, 24
See application file for complete search history.

(56) References Cited

U.S. PATENT DOCUMENTS

| | | | |
|---|---|---|---|
| 6,358,374 B1 | 3/2002 | Obee et al. | |
| 7,763,206 B2 * | 7/2010 | Mole | 422/4 |
| 2009/0252654 A1 * | 10/2009 | Hsu et al. | 422/122 |
| 2011/0033346 A1 | 2/2011 | Bohlen et al. | |

FOREIGN PATENT DOCUMENTS

| | | |
|---|---|---|
| CN | 1486746 A | 4/2004 |
| CN | 1522764 A | 8/2004 |
| CN | 101590256 A | 12/2009 |
| JP | 1-159030 A * | 6/1989 |
| JP | 1-159031 A * | 6/1989 |
| JP | 3-151023 A * | 6/1991 |
| JP | 6205930 A | 7/1994 |
| KR | 20030029415 A | 4/2003 |

* cited by examiner

*Primary Examiner* — Timothy Vanoy
(74) *Attorney, Agent, or Firm* — Ella Cheong Hong Kong; Sam T. Yip

(57) ABSTRACT

A system for air purification based on in-situ photocatalytic oxidation and ozonation includes a single multi-functional TiO2-based coating having photocatalytic activity for oxidation in the presence of a sufficient ozone supply and UV irradiation to synergistically oxidize gaseous pollutants at ambient conditions. Also disclosed is a method for removing gaseous pollutants using ozone and UV irradiation to simultaneously activate the photocatalytic oxidation in the presence of the TiO2-based coating to remove up to about 84% of the gaseous pollutants within 5 minutes.

16 Claims, 3 Drawing Sheets

SYSTEM AND METHOD FOR AIR PURIFICATION USING AN ENHANCED MULTI-FUNCTIONAL COATING BASED ON IN-SITU PHOTOCATALYTIC OXIDATION AND OZONATION

CROSS-REFERENCE TO RELATED APPLICATIONS

The present application claims priority of U.S. provisional application Ser. No. 61/457,058 filed Dec. 17, 2010, and the disclosure of which is hereby incorporated by reference.

FIELD OF THE INVENTION

The present invention relates to a system and method for air purification based on in-situ photocatalytic oxidation and ozonation. In particular, the present invention relates to a system including an enhanced multi-functional coating having a photo-catalytic activity in the presence of sufficient ozone supply and UV irradiation to remove gaseous pollutants, and the method thereof.

TECHNICAL BACKGROUND

Conventional air purifiers incorporated with an adsorbent bed to remove gaseous pollutants are usually short-lived and non-regenerative. That means regular replacement of the adsorbent bed is required. Obee et al. (U.S. Pat. No. 6,358,374) discloses an integrated air purification system including a catalyst bed, a UV source and a regenerable adsorbent bed to exert photocatalytic oxidation activity. It applies the concept of Langmuir-Hinshelwood kinetics to such a system so that the rate of oxidation is improved even in a relatively low level of gaseous contaminants. However, extra heat is required in the '374 system to release the captured contaminants from the regenerable adsorbent bed into a fixed volume of a compartment. Another disadvantage is that the oxidation rate resulting from the titanium dioxide-based catalyst in this system is limited by the species of contaminant, amount of each contaminant being adsorbed and the release rate of the adsorbed contaminants from adsorbent bed. It also cannot provide a continuous air purification system if the adsorbed contaminants reach the saturation level that would trigger the regeneration cycle of the adsorbent bed.

Bohlen et al. (US2011/0033346A1) also discloses an air cleaner channel in an air cleaner with a photocatalytic oxidation substrate being activated by UV-A illumination. The substrate includes three coatings of VOC decomposing catalyst, ozone decomposing catalyst and titanium oxide, respectively. Although the substrate has different coatings for different functions, the efficiency of photocatalytic oxidation of the gaseous pollutants and ozone decomposition is limited by the contacting surface of each coating with the corresponding gaseous pollutants or ozone. The airflow should pass through the three coatings of the substrate in order to remove the gaseous pollutant and excess ozone, and thus, there is a need in the art for a single multi-functional coating having at least photocatalytic oxidation and ozone decomposition activities and a large contacting surface area for air purification systems.

SUMMARY OF THE INVENTION

The first aspect of the present invention relates to a system for removing gaseous contaminants including an enhanced multi-functional coating for oxidizing the gaseous pollutants. The coating includes a single titanium dioxidetitanium dioxide ($TiO_2$)-based catalyst for enhancing the photocatalytic oxidation of the gaseous pollutants in the presence of sufficient ozone supply. In an exemplary embodiment, the $TiO_2$-based coating includes a plurality of mesoporous structures with a pore size of 2-20 nm in order to increase the total surface area of the catalyst (i.e. contacting surface). An ultraviolet irradiation source is also integrated into the system for activating the photocatalytic property of $TiO_2$ in order to carry out efficient oxidation in the presence of a sufficient ozone supply. The $TiO_2$-based coating can be activated simultaneously under UV light irradiation. Excess ozone is eliminated by the same multi-functional coating before the purified gases are exhausted from the system.

The second aspect of the present invention relates to a method for removing gaseous pollutant from gases in an indoor environment or gases from another source such as industrial effluent source. The method includes passing the polluted gases through a first filter including a mat of randomly arranged fibreglass to remove particulates. The filtered gases are then mixed with ozone in a mixer chamber. The mixture of the filtered gases and ozone is then subject to oxidation by passing the mixed gases through a second filter which includes an enhanced multi-functional coating. Under the UV irradiation, the photocatalytic property of the titanium dioxide-based coating is then activated to enhance oxidation in the presence of a sufficient ozone supply. At the same time, the excess ozone in the mixed gases is adsorbed on the surface of the multi-functional coating before the purified gases are exhausted. The adsorbed ozone is then eliminated in-situ to avoid any leakage to the environment after the oxidation. The purified gases are then exhausted, for example, to a space in which the purification system is located or to the atmosphere).

The system and method of the present invention is operated and carried out respectively under ambient conditions, i.e. room temperature, atmospheric pressure and relative humidity. The pollutant removal rate is from at least 82% to around 84% within 5 minutes of operation under continuous flow of air. The removable gaseous pollutants include but are not limited to $NO_x$, $SO_2$, $H_2S$, formaldehyde, $NH_3$. In addition to gaseous pollutants, volatile organic compounds (VOCs) and organic odors can also be removed by the system and method of the present invention.

DETAILED DESCRIPTION OF THE INVENTION

Figure 1:
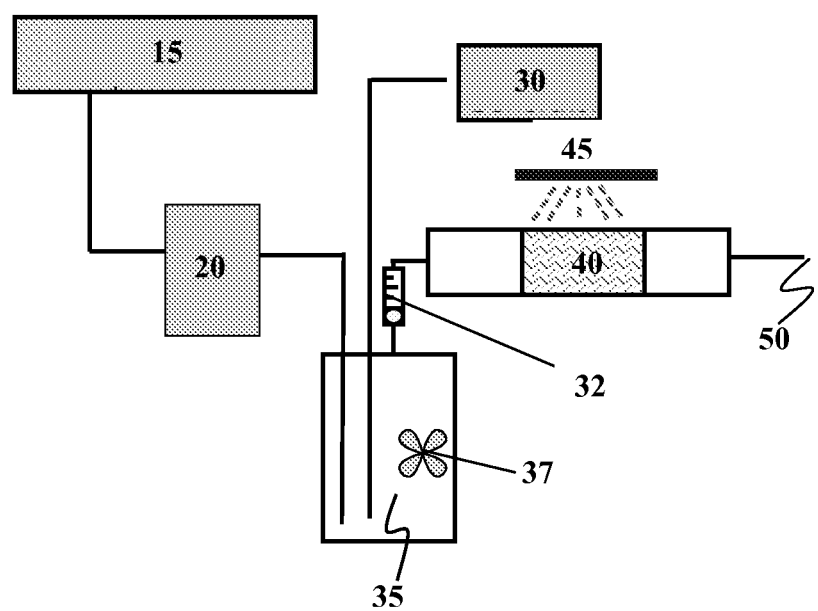
FIG. 1 is a schematic diagram of the system for removing gaseous pollutants according to the present invention.

FIG. 1 illustrates an air purification system 10 of the present invention and for efficiently removing gaseous pollutants from source 15 by using an enhanced photocatalytic coating together with the pre-treatment of ozone. In an exemplary embodiment, the system 10 includes a first filter 20 for removing relatively large and suspended particles such as dust particles. The first filter 20 can be any known mechanical or electrostatic filter, or a combination thereof to remove one or more types of large suspended particles such as particulates.

In an exemplary embodiment, the system is also connected to an ozone generator 30 to provide sufficient ozone gas to the system. In one embodiment, the ozone generator can be an external unit being connected to the system via a connecting pipe. In another embodiment, the ozone generator can be integrated into the system. The ozone generator can be an ozone lamp, ionizer, plasma discharging device, or any device that can generate ozone. The mechanism of generating ozone gas typically involves ionizing atmospheric oxygen ($O_2$) molecules into ozone molecules ($O_3$). Optionally, the ozone gas generated by the ozone generator is followed by using a zero air generator to dilute the ozone gas in order to provide an optimal ozone concentration. Ozone is a powerful oxidizer that can neutralize volatile organic compounds (VOCs) and also an anti-microbial agent to disrupt or lyse microorganisms such as bacteria. Ozone can also remove gaseous odors.

In an exemplary embodiment, the system also includes a mixer chamber 35 for receiving the filtered gases from the first filter 20 and mixing the ozone gas from the ozone generator 30. The main purpose of mixing the filtered gases with the ozone gas is to provide a sufficient ozone source for oxidization at a second filter 40 which includes the $TiO_2$-based multi-functional coating of the present invention. In a preferred embodiment, the concentration of ozone gas is about 5 ppm and the retention time of mixing the ozone gas with the polluted gases is about 20 seconds in the mixing chamber 35. The mixing chamber 35 is preferably made of stainless steel to avoid any oxidation of the inner contact surface by the ozone gas. The mixing chamber 35 is also preferably incorporated with a mixer chamber fan 37 rotating at about 600 rpm to facilitate the mixing of the ozone gas with the polluted gases in the mixing chamber 35. The flow rate of the mixed gas from the mixing chamber 35 to the second filter 40 is further monitored by a flow meter 32 being connected to the mixing chamber 35 at one end and to the second filter 40 at the other end. Ozone in the mixer chamber 35 can also carry out minimal oxidization of the gaseous pollutants before passing to the second filter 40. Excess ozone will be eliminated by the surface photocatalytic reactions of the same coating in-situ at the later stage by the second filter 40.

Depending upon the overall configuration of air purification system 10, various fans such as the mixer chamber fan 37 can be positioned at locations throughout the system 10 to efficiently move contaminated air through the system 10 at an appropriate volume to facilitate contaminant removal. Similarly, more than one flow meter 32 can be positioned at different locations throughout the system 10 to monitor the flow rate of different gases.

After the filtered gases are mixed with ozone gas in the mixer chamber 35, the mixed gases pass through the flow meter 32 to the second filter 40 which incorporates a single layer of photocatalytic coating based on titanium dioxide ($TiO_2$). In an exemplary embodiment, the $TiO_2$-based coating includes titanium dioxide and optionally includes one or more metal selected from Ti, Zn, Cu, La, Mo, W, V, Se, Ba, Ce, Sn, Fe, Mg or Al and/or alloys and/or oxides thereof. The photocatalytic property of the $TiO_2$-based coating is activated by irradiation from a UVA light tubes with an intensity of 500 $\mu W/cm^2$ 45. This UVA light source can be a UV light bulb, UV LED or any source which can emit UV irradiation with wavelength from 320 nm to 400 nm, more preferably at 365 nm. The $TiO_2$-based coating activates the second oxidation of gaseous pollutant in the presence of a sufficient ozone supply and UV irradiation. Another function of the coating is to eliminate the excess ozone because such coating also has ozone-decomposing activity. In-situ elimination of excess ozone can avoid the leakage of these reactive molecules together with the purified gases. After passing through the second filter 40, the purified gases are ready to be exhausted back to the same indoor environment from where the polluted gases are collected or to another environment such as another enclosed environment or the atmosphere via exhaust 50.

The method for removing gaseous pollutants of the present invention follows a substantially similar workflow of the system as described in FIG. 1. However, it is understood that any modifications in the system which can result in the same technical effect according to the method of the present invention will still fall within the scope of the invention.

In an exemplary embodiment, the method for purifying polluted gases includes: (i) collecting the polluted gases from a source or from an indoor environment to a first filter; (ii) filtering large suspended particles through the first filter; (iii) passing the filtered gases to a mixer chamber to mix the filtered gases with ozone gas generated from an ozone generator; (iv) passing the mixed gases from the mixer chamber to a second filter incorporating a single multi-functional coating; (v) irradiating the single multi-functional coating by a UV source to oxidize the gaseous pollutant and simultaneously eliminate the excess ozone from the mixed gases by the same single multi-functional coating in order to obtain purified gases; (vi) exhausting the purified gases from the second filter to the same indoor environment by circulation or to another enclosed area or to the atmosphere. In a preferred embodiment, the method is carried out under the ambient conditions. Ambient conditions refer to ambient temperature, atmospheric pressure and relative humidity of the location where the method is carried out or the atmosphere. In other embodiment, the method is suitable for use in different conditions such as high temperature, high atmospheric pressure and/or higher relative humidity if necessary. In those situations, additional methods for removing moisture or excess heat from the input gas stream can be incorporated in the overall process.

Figure 2A:
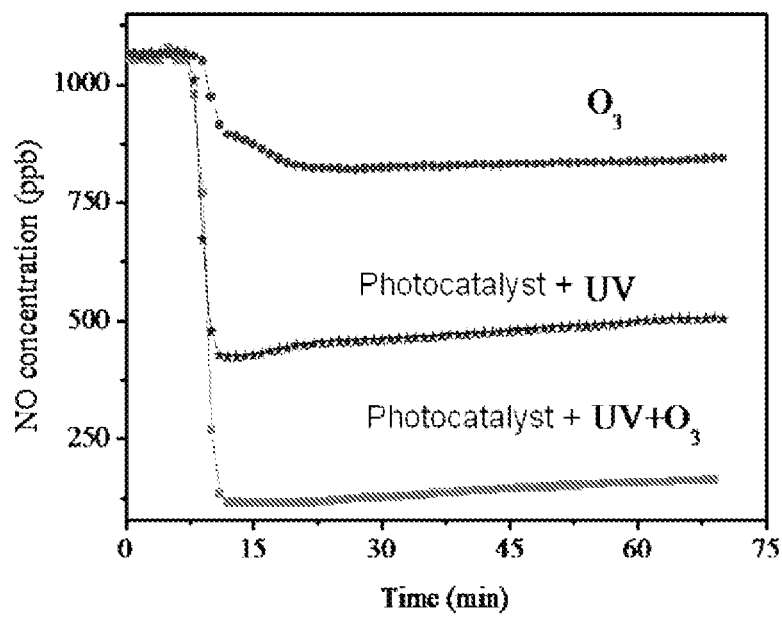
FIG. 2 is a comparison of the elimination rate of nitrogen monoxide (NO) (2A) and the production rate of nitrogen dioxide ($NO_2$) (2B) for different conditions: (i) UV irradiation alone; (ii) ozone alone; (iii) a combination of UV irradiation and ozone.
Figure 2B:
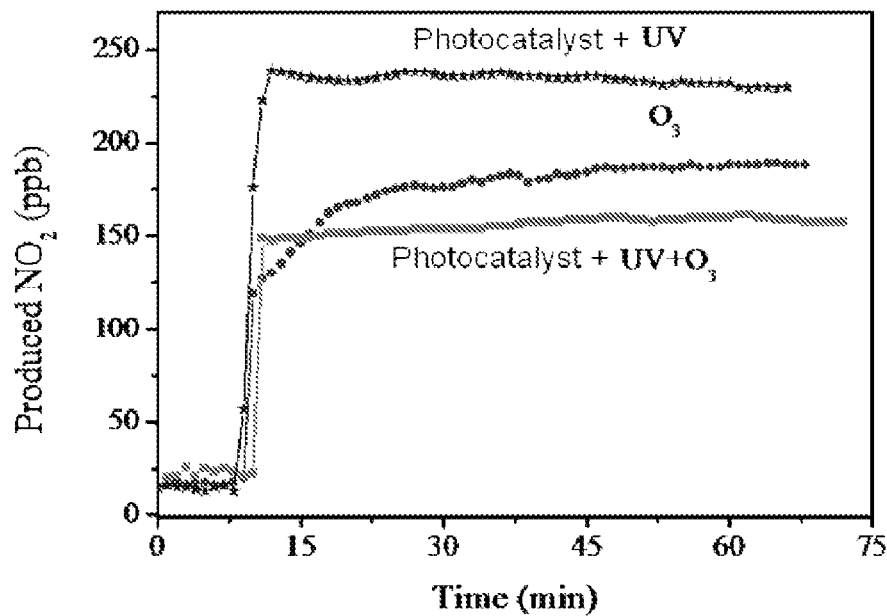

FIG. 2 is a graph showing the result of a test to compare the elimination of an example pollutant, nitrogen monoxide (NO) (FIG. 2A), and the production of nitrogen dioxide ($NO_2$) (FIG. 2B) versus time by using the system of the present invention under different conditions. These conditions are: (i) ozone alone; (ii) UV alone; and (iii) a combination of ozone and UV. In this test, a gas sample with a pre-determined concentration of target pollutant is provided to the system of the present invention. The gas sample is continuously collected at the downstream portion of the system over a period of time, e.g. 1 hour, to measure the concentration of NO and $NO_2$ at each time interval. The concentration of NO and $NO_2$ reflect the oxidation efficiency of the system in different conditions.

In FIG. 2A, the NO concentration under the treatment of ozone alone is reduced by around 16-18% while the NO concentration under the treatment of UV irradiation alone is reduced by around 63-65% within the first 15 minutes of the test. As compared to these single source treatments, the NO concentration under a combined treatment of UV and ozone is reduced by around 82-84% within the first 5 minutes. The result demonstrates that the system incorporating the multi-functional coating of the present invention can significantly reduce the level of pollutants such as NO under the combined treatment of UV and ozone. This also demonstrates that the synergetic effect of ozone and UV in the presence of the multi-functional coating.

In FIG. 2B, the $NO_2$ concentration remains at the relative low level until a later point within the first 15 minutes of the test. Since that point, the rate of conversion from NO to harmful $NO_2$ starts to rise when the photocatalytic oxidation takes place at the multi-functional coating. In comparison, the production of $NO_2$ by the UV treatment alone is the highest due to the lack of external ozone supply (only limited numbers of $O^-$ free radicals are generated by the irradiation of UV); the production of $NO_2$ by the ozone treatment alone is the second highest among the three; the production $NO_2$ by the combination of ozone and UV treatments is the lowest. In conclusion, in the presence of both ozone and UV irradiation, the conversion of NO to harmful $NO_2$ is the lowest because most of the NO appears to be primarily oxidized by the multi-functional $TiO_2$-based coating of the present invention into nitrates and therefore the amount of $NO_2$ converted from NO is low. In addition, the $NO_2$ can be further oxidized by ozone to form nitrates. Thus, the total concentration of harmful NO and $NO_2$ is the lowest in the presence of both ozone and UV irradiation.

Figure 3A:
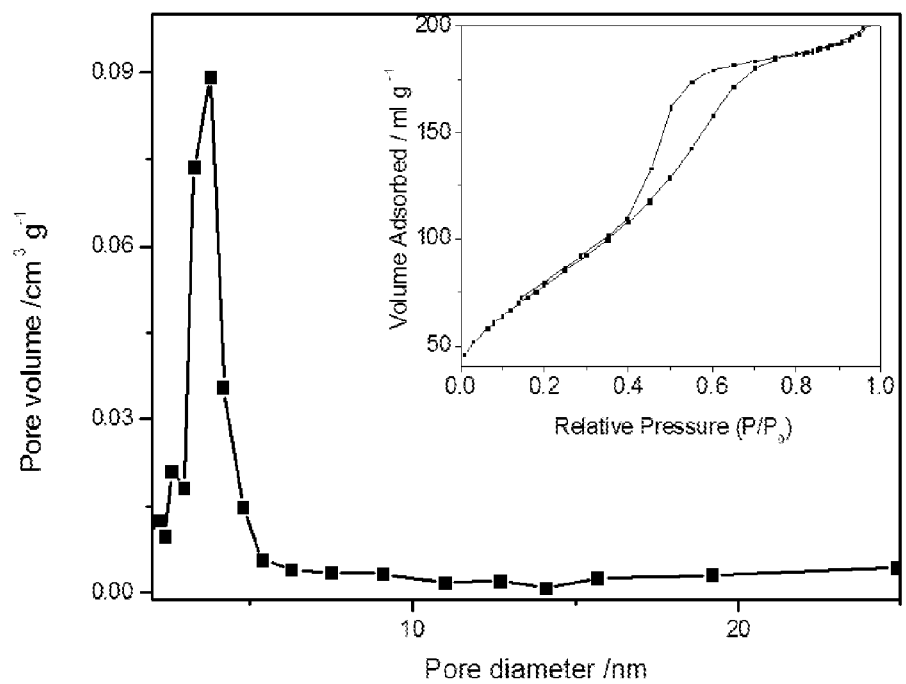
FIG. 3A is a pore size distribution of mesoporous $TiO_2$ thin film by BET surface analysis.
Figure 3B:
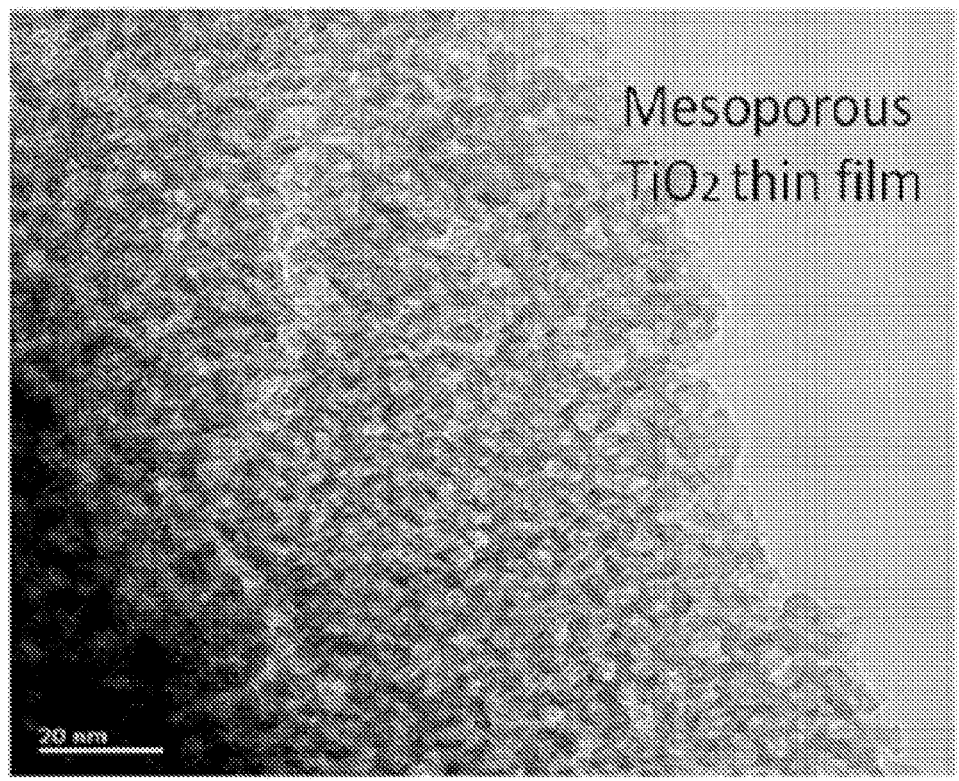
FIG. 3B is a TEM image of mesoporous $TiO_2$ thin films on foam ceramic filter.

FIG. 3A shows that the pore size distribution of mesoporous $TiO_2$ thin film. The pore size of TiO2 thin film is around 4 nm. FIG. 3B shows the image of $TiO_2$ thin films composed of small particles with the pore size of around 4-5 nm. The mesoporous $TiO_2$ coating does not only have large surface area and keep high photocatalytic activity but it can offer more active sites for carrying out catalytic reactions in air purification.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

INDUSTRIAL APPLICABILITY

Compared to conventional air purifiers, the present system incorporating a multi-functional coating in combination with both ozone and UV irradiation provides the following features in one unit: (1) enhance efficiency of oxidation, (2) converting gaseous pollutant into harmless gases to both human body and our environment, and (3) comparatively durable, less costly and compatible single catalyst coating for multiple functions. It is suitable for mass production for various applications such as in air conditioning systems, humidifiers and dehumidifiers, industrial processes requiring air purification and control of ozone exhaustion.

What we claim:

1. A system for removing particulates and gaseous pollutants of an airflow comprising:
   a first filter for removing large suspended particles from said airflow to create a first filtered gas;
   a mixer chamber for mixing the first filtered gas with ozone gas to create an ozone-enriched first filtered gas;
   an ozone generator for providing said ozone gas to said mixer chamber;
   a second filter incorporating a single multi-functional $TiO_2$-based coating; and
   a UV generator for generating UV in the presence at said second filter incorporating the $TiO_2$-based coating,
   wherein the placement of the mixer chamber, the UV generator, and the $TiO_2$-based coating is configured to expose the ozone-enriched first filtered gas to the simultaneous effects of the multi-functional $TiO_2$-based coating and UV light generated by the UV generator, and wherein said UV generator is selected from UV lamp or UV LED to emit the UV light at a wavelength of 320 nm to 400 nm, and wherein said ozone and UV light act synergistically at said second filter in the presence of said multi-functional $TiO_2$-based coating including a plurality of mesoporous structures which are in contact with said ozone-enriched first filtered gases in order to oxidize about 82% to about 84% of said gaseous pollutants into harmless gases within 5 minutes.

2. The system according to claim 1, wherein said first filter comprises a mat of randomly arranged fibreglass.

3. The system according to claim 1, wherein said mixer chamber is made of stainless steel.

4. The system according to claim 1, wherein said ozone generator is either external to said mixer chamber or integrated into said mixer chamber, and said ozone generator is selected from an ionizer, plasma discharging source, or a combination thereof.

5. The system according to claim 1, wherein said mixed chamber comprises a ventilator rotating at a rate of 600 rpm for mixing the filtered gases from said first filter with said ozone from said ozone generator for 20 seconds.

6. The system according to claim 1, wherein said multi-functional $TiO_2$-based coating is a photocatalyst of oxidation and further comprises one or more of Ti, Zn, Cu, La, Mo, W, V, Se, Ba, Ce, Sn, Fe, Mg or Al, or oxides thereof, or alloys thereof.

7. The system according to claim 1, wherein said multi-functional coating is an ozone-decomposing element and further comprises one or more of Ti, Zn, Cu, La, Mo, W, V, Se, Ba, Ce, Sn, Fe, Mg or Al, or oxides thereof, or alloys thereof.

8. The system according to claim 1, wherein each of said plurality of mesoporous structures has a pore size of 2-20 nm.

9. The system according to claim 1, wherein the excess ozone of said ozone after oxidation is decomposed by said multi-functional coating.

10. The system according to claim 1, wherein said gaseous pollutants comprises $NO_x$, $SO_2$, $H_2S$, formaldehyde, $NH_3$, VOCs, ozone and odors.

11. The system according to claim 1, wherein any part of said system operates under ambient condition.

12. A method for removing particulates and gaseous pollutants of an airflow comprising:
   collecting said airflow from an indoor environment or from an external source to create a collected gas;
   filtering the collected gas by a first filter to remove large suspended particles to create a first filtered gas;
   mixing the first filtered gases with ozone generated from an ozone generator to create an ozone-enriched first filtered gas;
   oxidizing the ozone-enriched first filtered gas by a second filter incorporating a multi-functional $TiO_2$-based coating and a UV source at a wavelength of 320 nm to 400 nm;
   eliminating excess ozone after said oxidizing at said second filter to create a purified gases; and exhausting the purified gases back to said indoor environment or to where said airflow comes from or to the atmosphere, wherein said oxidizing is a result of said ozone and UV light generated by said UV source acting synergistically in the presence of said multi-functional $TiO_2$-based coating to reduce the level of said gaseous pollutants by about 82% to about 84% within 5 minutes.

13. The method of claim 12, wherein said filtering of said collected gases is by passing through said first filter comprising a mat of randomly arranged fibreglass in order to remove large suspended particles including said particulates to create said first filtered gas.

14. The method of claim 12, wherein said mixing of said first filtered gases comprises providing ozone gas from an ozone generator to said mixer chamber at a rate of 600 rpm for 20 seconds at ambient temperature, atmospheric pressure and relative humidity.

15. The method of claim 12, wherein said eliminating of said excess ozone is performed in-situ by said multi-functional $TiO_2$-based coating after said oxidizing at ambient temperature, atmospheric pressure and relative humidity.

16. The method of claim 12, wherein said oxidizing is further enhanced by increasing the total surface area of said multi-functional $TiO_2$-based coating comprising a plurality of mesoporous structures with a pore size of 2-20 nm such that about 82% to 84% of said gaseous pollutants are removed within 5 minutes.

* * * * *